United States Patent [19]

Picard et al.

[11] Patent Number: 4,761,419

[45] Date of Patent: Aug. 2, 1988

[54] 6-(((SUBSTITUTED)QUINOLINYL)ETHYL)- AND ETHENYL)TETRAHYDRO-4-HYDROXYPYRAN-2-ONE INHIBITORS OF CHOLESTEROL BIOSYNTHESIS

[75] Inventors: Joseph A. Picard; Bruce D. Roth, both of Ann Arbor; Drago R. Sliskovic, Ypsilanti, all of Mich.

[73] Assignee: Warner-Lambert Company, Morris Plains, N.J.

[21] Appl. No.: 129,516

[22] Filed: Dec. 7, 1987

[51] Int. Cl.$^4$ .................... A61K 31/34; A61K 31/47; C07D 217/12; C07D 217/14

[52] U.S. Cl. .................................. 514/311; 514/256; 514/314; 546/167; 546/171; 546/173; 546/174; 546/175; 544/333

[58] Field of Search ............... 546/167, 171, 173, 174, 546/175; 544/333; 514/311, 314, 256

[56] References Cited

U.S. PATENT DOCUMENTS

| | | | |
|---|---|---|---|
| 4,198,425 | 4/1980 | Mistui et al. | 424/279 |
| 4,255,444 | 3/1981 | Oka et al. | 424/279 |
| 4,262,013 | 4/1981 | Mistui et al. | 424/279 |
| 4,375,475 | 3/1983 | Willard et al. | 424/279 |
| 4,613,610 | 9/1986 | Wareing | 514/406 |
| 4,647,576 | 3/1987 | Hoefle et al. | 514/422 |
| 4,668,794 | 5/1987 | Wareing | 548/342 |
| 4,681,893 | 7/1987 | Roth | 514/422 |

OTHER PUBLICATIONS

PCT International Application No. PCT/EP83/00308 Pub. No. WO 84/02131.

Primary Examiner—Mary C. Lee
Assistant Examiner—J. Richter
Attorney, Agent, or Firm—Jerry F. Janssen

[57] ABSTRACT

Certain trans-6-[[(substituted)quinolinyl]ethyl]-and ethenyl]tetrahydro-4-hydroxypyran-2-ones and the corresponding dihydroxy ring-opened acids derived therefrom are potent inhibitors of the enzyme 3-hydroxy-3-methylglutaryl-coenzyme A reductase (HMG-CoA reductase) and are useful as hypocholesterolemic and hypolipidemic agents.

15 Claims, No Drawings

6-(((SUBSTITUTED)QUINOLINYL)ETHYL)- AND ETHENYL)TETRAHYDRO-4-HYDROXYPYRAN-2-ONE INHIBITORS OF CHOLESTEROL BIOSYNTHESIS

BACKGROUND OF THE INVENTION

The present invention is related to compounds and pharmaceutical compositions useful as hypocholesterolemic and hypolipidemic agents. More particularly, this invention concerns certain trans-6-[[(substituted)-quinolinyl]ethyl]- and ethenyl]tetrahydro-4-hydroxypyran-2-ones and the corresponding dihydroxy ring-opened acids which are potent inhibitors of the enzyme 3-hydroxy-3-methylglutaryl-coenzyme A reductase (HMG-CoA reductase), pharmaceutical compositions containing such compounds, and a method of lowering blood serum cholesterol levels employing such pharmaceutical compositions.

High levels of blood cholesterol and blood lipids are conditions which are involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine* (1981), 305, No. 9, 515-517). It has now been established that lowering LDL-C levels affords protection from coronary heart disease (cf. *Journal of the American Medical Association* (1984) 251, No. 3, 351-374).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer et al, *Proc. Soc. Exper. Biol. Med.* (1959), 102, 270) and F. H. Hulcher, *Arch. Biochem. Biophys.*, 30 (1971), 146, 22.

U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown et al, *J. Chem. Soc. Perkin I*, (1976), 1165.

U.S. Pat. No. 4,255,444 to Oka et al, discloses several synthetic derivatives of mevalonolactone having antilipidemic activity.

U.S. Pat. Nos. 4,198,425 and 4,262,013 to Mitsue et al, disclose aralkyl derivatives of mevalonolactone which are useful in the treatment of hyperlipidemia.

U.S. Pat. No. 4,375,475 to Willard et al, discloses certain substituted 4-hydroxytetrahydropyran-2-ones which, in the 4(R)-trans stereoisomeric form, are inhibitors of cholesterol biosynthesis.

U.S. Pat. No. 4,647,576 to Hoefle, et al, discloses certain trans-6-[2-[(substituted)-pyrrol-1-yl]-]alkyltetrahydro-4-hydroxypyran-2-ones and the corresponding lactone ring-opened acids as inhibitors of cholesterol biosynthesis.

U.S. Pat. No. 4,681,893 to Roth discloses certain trans-6-[[(2-, (3-, or (-carboxamido-substituted)pyrrol-1-yl]alkyl- or alkenyl]-tetrahydro4-hydroxypyran-2-one inhibitors of cholesterol biosynthesis.

SUMMARY OF THE INVENTION

In accordance with the present invention, there are provided certain trans-6-[[2-(substituted)quinolinyl]-ethyl- or ethenyl]tetrahydro-4-hydroxypyran-2-ones and the corresponding ring-opened hydroxy-acids which are potent inhibitors of cholesterol biosynthesis by virtue of their ability to inhibit the enzyme 3-hydroxy-3methylglutaryl coenzyme A reductase (HMG-CoA reductase).

In particular, in its broadest chemical compound aspect, the present invention provides compounds of structural Formula I

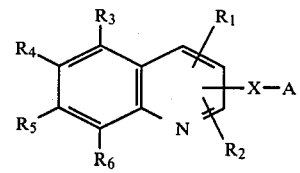

wherein A is

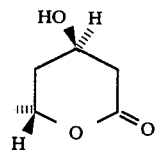

and X is —CH2CH2— or —CH=CH— (preferably in the trans configuration).

$R_1$ and $R_2$ are independently hydrogen; alkyl of from one to six carbons; trifluoromethyl; cyclopropyl; cyclohexyl; cyclohexylmethyl; phenyl; phenyl substituted with fluorine, chlorine, bromine, hydroxy, trifluoromethyl, alkyl of from one to four carbon atoms, or alkoxy of from one to four carbon atoms; phenylmethyl; phenylmethyl substituted with fluorine, chlorine, bromine, hydroxy, trifluoromethyl, alkyl of from one to four carbon atoms, or alkoxy of from one to four carbon atoms; 2-, 3-, or 4-pyridinyl; or 2-, -, or 5-pyrimidinyl; provided that when X is in the 2-position, $R_1$ is hydrogen and is attached in the 4-position.

$R_3$, $R_4$, $R_5$, and $R_6$ are independently selected from hydrogen; alkyl of from one to six carbon atoms; trifluoromethyl; cyclopropyl; fluorine; chlorine; bromine; hydroxy; alkoxy of from one to four carbon atoms; cyano; nitro; amino; acetylamino; aminomethyl; phenyl; phenyl substituted with fluorine, chlorine, bromine, hydroxy, trifluoromethyl, alkyl of from one to four carbon atoms, or alkoxy of from one to four carbon atoms; phenylmethyl; or phenylmethyl substituted with fluorine, chlorine, bromine, hydroxy, trifluoromethyl, or alkyl of from one to four carbon atoms.

Also contemplated as falling within this aspect of the invention are the corresponding dihydroxy-acid compounds of Formula II corresponding to the opened form of the lactone ring of compounds of Formula I

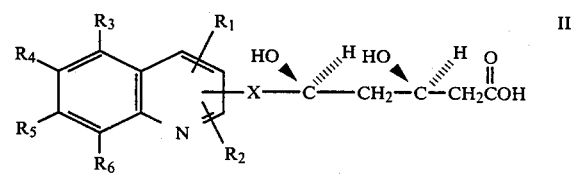

where X, $R_1$, $R_2$, $R_3$, $R_4$, $R_5$, and $R_6$ are as defined above, and the pharmaceutically acceptable salts thereof, all of the compounds being in the trans racemate of the tetrahydropyran moiety.

In another aspect of the present invention, there is provided a method of preparing compounds of Formula I above by (a) first reacting a substituted [(quinolin-3-yl)ethyl- or ethenyl]aldehyde compound of Formula III

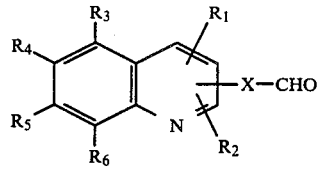

where are X, R₁, R₂, R₃, R₄, R₅, and R₆ as defined above, with the alkali metal salt of the dianion of ethyl acetoacetate to form a compound of structural Formula IV

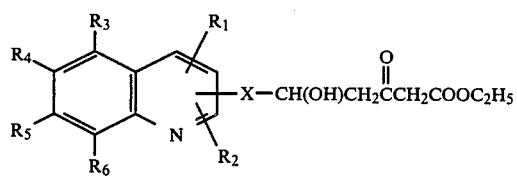

where X, R₁, R₂, R₃, R₄, R₅, and R₆ are as defined above, then successively (b) reducing Compound IV with a trialkylborane and sodium borohydride and (c) oxidizing with alkaline hydrogen peroxide to produce an ester compound of Formula V

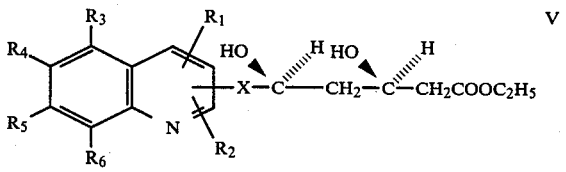

and finally (d) hydrolyzing and cyclizing, if desired, the ester compound of Formula V to a lactone compound of Formula I by heating in an inert solvent or, alternatively converting, if desired, the intermediate dihydroxy acid thus formed to a pharmaceutically acceptable salt.

In another aspect, the present invention provides pharmaceutical compositions, useful as hypolipidemic or hypocholesterolemic agents, comprising a hypolipidemic or hypocholesterolemic affective amount of a compound in accordance with this invention as set forth above, in combination with a pharmaceutically acceptable carrier.

In another aspect, the present invention provides a method of inhibiting cholesterol biosynthesis in a patient in need of such treatment by administering a pharmaceutical composition in accordance with the present invention as defined above.

DETAILED DESCRIPTION

The compounds of the present invention form a class of substituted quinolines in which the quinoline moiety

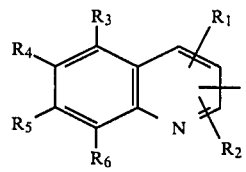

is substituted at the 2-, 3-, or -position with the group

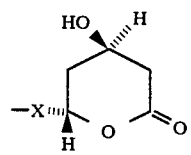

where X is as previously defined. Compounds in which X is attached at position 2 and groups other than hydrogen are attached at position 4 of the quinolinyl moiety are difficult to synthesize, and are thus excluded from the scope of this invention.

Preferred compounds of the invention are those in which the position of attachment of the ethyl- or ethenyl-lactone ring is at position 3 of the quinolinyl moiety. Preferred substituent groups for R₁ and R₂ are phenyl, substituted phenyl, and lower alkyl, most preferably isopropyl.

As used throughout this specification and the appended claims, the term "alkyl" denotes a branched or unbranched saturated hydrocarbon group derived by the removal of one hydrogen atom from an alkane. The term "lower alkyl" denotes alkyl of from one to four carbon atoms.

The term "alkoxy" denotes an alkyl group, as just defined, attached to the parent molecular residue through an oxygen atom.

Particularly preferred compounds of the present invention include the following:

[4α,6β(E)]6-[2-[6-Chloro--(4-fluorophenyl)-2-methyl-3-quinolinyl]ethenyl]tetrahydro-4-hydroxy-2H-pyran-2-one.

[4α,6β(E)]6-[2-[6-Chloro-4-(-fluorophenyl)-2-(1-methylethyl)-3-quinolinyl]ethenyl]tetrahydro-4-hydroxy2H-pyran-2-one.

[4α,6β(E)]6-[2-[2-[6-(-4Fluorophenyl)-2-(1-methylethyl)-3-quinolinyl]ethenyl]tetrahydro-4-hydroxy-2H-pyran-2-one.

[R*,S*-(E)]-7-[6-Chloro-4-(4-fluorophenyl)-2-methyl-3-quinolinyl]-3,5-dihydroxy-6-heptenoic acid.

[R*,S* -(E)]-7-[6-Chloro-4-(4-fluorophenyl)-2-(1-methylethyl)-3-quinolinyl]-3,5-dihydroxy-6-heptenoic acid.

[R*,S*-(E)]-7-[4-(4-Fluorophenyl)-2-(1-methylethyl)-3-quinolinyl]-3,5-dihydroxy-6-heptenoic acid.

Compounds of the present invention in which the ethyl- or ethenyl-lactone moiety is attached to position 3 of the quinolinyl moiety are prepared by the general synthetic methods outlined in Reaction Sequence 1.

Compounds of the present invention where the ethyl- or ethenyl-lactone moiety is attached to the 2- or 4-position of the quinolinyl moiety are prepared by the general synthetic methods outlined in Reaction Sequence 2.

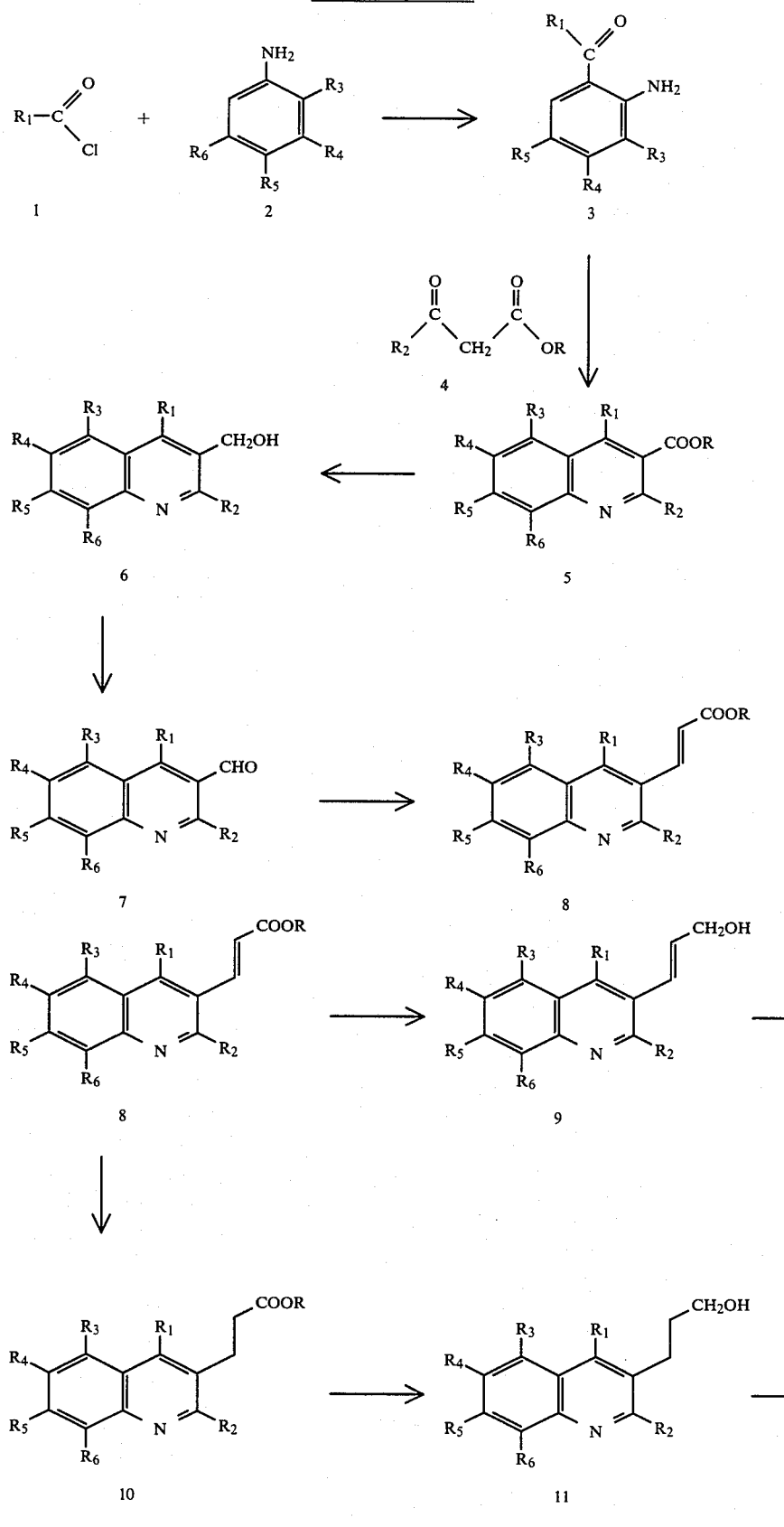

-continued
Reaction Sequence 1

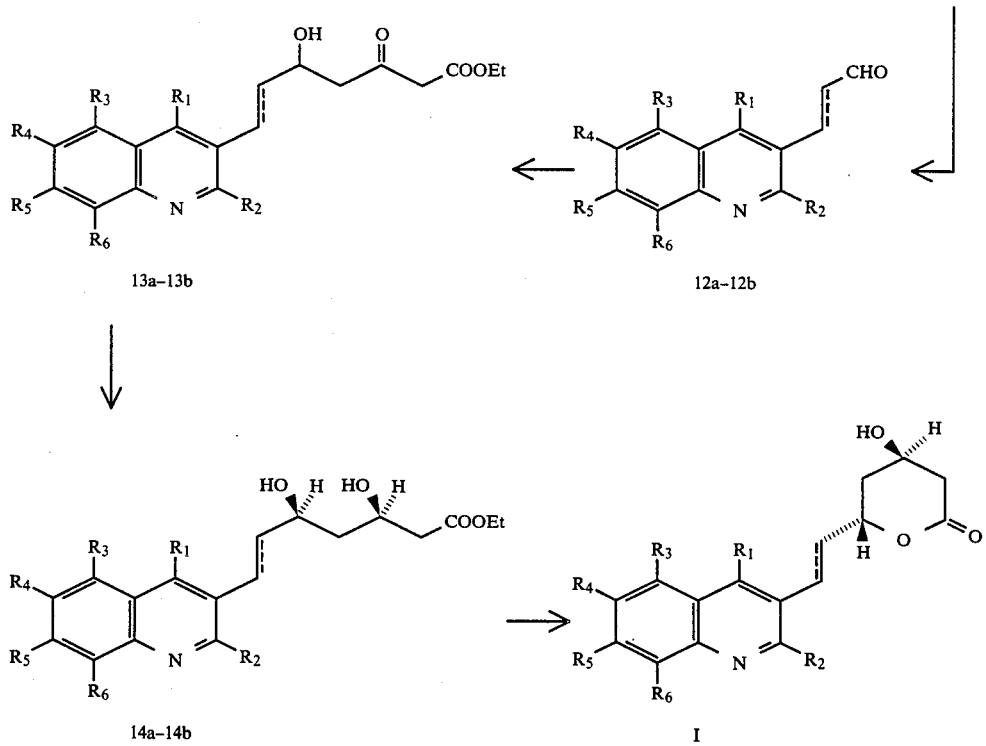

Referring to Reaction Sequence 1, the acid chloride, 1 having the desired substituent group $R_1$, is reacted with the appropriately 2,3,4,5-substitued aniline, 2, in the presence of zinc chloride at a temperature of about 200° C., and the resulting reaction mixture hydrolyzed with acetic and hydrochloric acids to produce the substituted aclamine, 3.

The acylamine, 3, is reacted with the desired β-keto-ester, 4, in the presence of p-toluenesulfonic acid, an the intermediate thus formed is dehydrated and cyclized to the substituted quinoline-3-carboxylic acid ester, 5, by heating in toluene under reflux.

The ester, 5, is reduced at −78° C. by the action of diisobutylaluminum hydride ("DIABL") to yield the alcohol, 6. The alcohol, 6, is then oxidized to the corresponding aldehyde, 7, by the method of Swern (Swern, et al, *J. Org. Chem.*, 43:2480 (1978)) to yield the desired aldehyde, 7.

Wittig reaction of the aldehyde, 7, with an ylide such as carbomethoxy triphenylphosphorane in methylene chloride at room temperature produces the unsaturated trans-ester, 8, in high yield. T ester, 8, is reduced to the allyl alcohol, 9, using a well-known procedure employing two equivalents of diisobutyl aluminum hydride at −78° C.

Alternatively, the unsaturated ester, 8, is reduced over Pd/C by the action of hydrogen to produce the saturated ester, 10, which is then reduced by the action of DIBAL to produce the corresponding alcohol which may then be carried forward in the sequence of steps to finally produce the product having the saturated ethyl bridge (X=ethylene in generic Formula I).

The alcohols, 9 or 11, are reoxidized to the corresponding aldehydes, 12a or 12b, by Swern oxidation, followed by an aldol condensation with the sodium lithium dianion of ethyl acetoacetate at −78° C. in tetrahydrofuran (See Kraus, et al, *J. Org. Chem.*, 48:2111 (1983)) to form the 5-hydroxy-3-oxo-6-heptenoic esters 13a and 13b.

The product of this condensation is then reduced in a sequence of steps in which it is first dissolved in a polar solvent such as tetrahydrofuran under a dry atmosphere. A small excess of triethylborane and catalytic amounts of 2,2-dimethylpropanoic acid are next added. The mixture is stirred at room temperature for a short period, after which it is cooled to a temperature preferably between about −60° C. and −80° C. Dry methanol is added, followed by sodium borohydride. The mixture is kept at low temperature for 4–8 hours before treating it with hydrogen peroxide and ice water. The substituted 3,5-dihydroxy-6-heptenoic acid ethyl esters, 14a and 14b, are isolated having the preferred R*,S* and R*,R* configurations, respectively.

The esters, 14a and 14b may be utilized as such in the pharmaceutical method of this invention, or may be converted, if desired, to the corresponding acid salt forms, such as the sodium salt, employing basic hydrolsis by generally well-known methods. The free acids, produced by acidification of the sodium salts, can be dehydrated to the lactones, I by heating the acids in an inert solvent such as toluene with concomitant azeotropic removal of water.

Referring to Reaction Sequence 2, the substituted isatin 15, is condensed by the Pfitzinger Reaction (see W. Pfitzinger, *J. Prakt. Chem.*, [2]3:100 (1886); 38:582 (1888)) with the oxime, 16, to produce the substituted quinoline-4-carboxylic acid, 17. Alternatively, the potassium salt of 17 (prepared by the treatment of acid, 17, with potassium hydroxide in

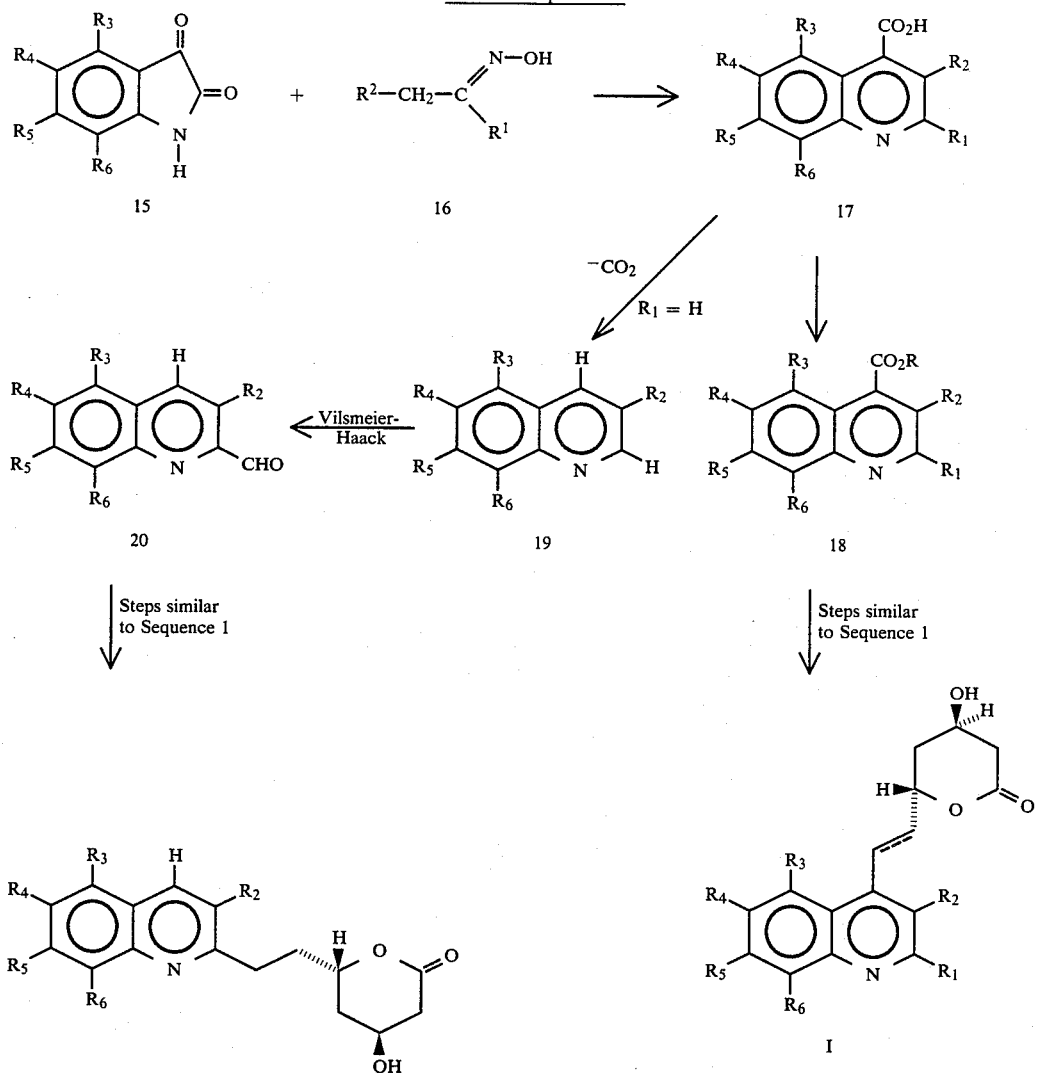

Reaction Sequence 2 methanol) is esterified by heating a tetrahydrofuran solution of the salt of 17 with ethyl iodide at a temperature of about 70° C. The resulting ethyl ester, 18, is then carried throuh a series of reaction steps analogous to those discussed above in Reaction Sequence 1 to produce the compounds of Formula I.

The acid, 17, is decarboxylated by heating to the corresponding quinoline, 19, which is then converted to the quinoline-2-carboxaldehyde, 20, by the Vilsmeier-Haack formylation reaction (see A. Vilsmeier, et al, Ber., 60:119 (1927)).

The aldehyde, 20, is then carried through a series of reaction steps analogous to those discussed above in Reaction Sequence 1 to produce the compounds of Formula I.

In the ring-opened dihydroxy acid form, compounds of the present invention react to form salts with pharmaceutically acceptable metal and amine cations formed from organic and inorganic bases.

The term "pharmaceutically acceptable metal cation" contemplates positively charged metal ions derived from sodium, potassium, calcium, magnesium, aluminum, iron, zinc and the like.

The term "pharmaceutically acceptable amine cation" contemplates the positively charged ions derived from ammonia and organic nitrogenous bases strong enough to form such cations. Bases useful for the formation of pharmaceutically acceptable nontoxic base addition salts of compounds of the present invention form a class whose limits are readily understood by those skilled in the art. (See, for example, Berge, et al, "Pharmaceutical Salts," *J. Pharm. Sci.*, 66:1–19 (1977)).

The free acid form of the compound may be regenerated from the salt, if desired, by contacting the salt with a dilute aqueous solution of an acid such as hydrochloric acid.

The base addition salts may differ from the free acid form of compounds of this invention in such physical characteristics as melting point and solubility in polar solvents, but are considered equivalent to the free acid forms for purposes of this invention.

The compounds of this invention can exist in unsolvated as well as solvated forms. In general, the solvated forms, with pharmaceutically acceptable solvents such as water, ethanol, and the like, are equivalent to the unsolvated forms for purposes of this invention.

The compounds of this invention are useful as hypocholesterolemic or hypolipidemic agents by virtue of their ability to inhibit the biosynthesis of cholesterol through inhibition of the enzyme 3-hydroxy-3-methylglutaryl-coenzyme A reductase (HMG-CoA reductase).

The ability of compounds of the present invention to inhibit the biosynthesis of cholesterol was measured by a method (designated CSI screen) which utilizes the procedure described by R. E. Dugan et al, *Archiv. Biochem. Biophys.*, (1972), 152, 21–27. In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of 14C-acetate into nonsaponifiable lipid by the rat liver homogenate is measured. The micromolar concentration of compound required for 50% inhibition of sterol synthesis over a one-hour period is measured, and expressed as an IC50 value.

The activities of several representative examples of compounds in accordance with the present invention appear in Table 1.

TABLE 1

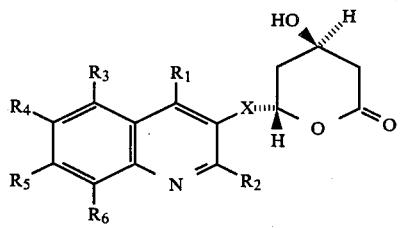

| X | $R_1$ | $R_2$ | $R_3$ | $R_4$ | $R_5$ | $R_6$ | CSI $IC_{50}$ $\mu$Mole/Liter |
|---|---|---|---|---|---|---|---|
| —CH=CH— | 4-Fluorophenyl | —CH$_3$ | H | Cl | H | H | 0.35 |
| —CH=CH— | 4-Fluorophenyl | —CH(CH$_3$)$_2$ | H | Cl | H | H | 0.032 |

For preparing pharmaceutical compositions from the compounds described by this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with finely divided active compound. In tablets, the active compound is mixed with the carrier having the necessary binding properties in suitable proportions and compacted in the shape and size desired.

For preparing suppository preparations, a low-melting wax such as a mixture of fatty-acid glycerides and cocoa butter is first melted, and the active ingredient is dispersed homogeneously therein, as by stirring. The molten homogeneous mixture is then poured into convenient sized molds and allowed to cool and solidify.

The powders and tablets preferably contain 5 to about 70% of the active ingredient. Suitable solid carriers are magnesium carbonate, magnesium stearate, talc, sugar, lactose, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as carrier providing a capsule in which the active component (with or without other carriers) is surrounded by a carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions for oral use can be prepared by dissolving the active component in water and adding suitable colorants, flavoring agents, stabilizers, and thickening agents as desired. Aqueous suspensions for oral use can be made by dispersing the finely divided active component in water with viscous material, i.e., natural or synthetic gums, resins, methyl, cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

In therapeutic use as hypolipidemic or hypocholesterolemic agents, the compounds utilized in the pharmaceutical method of this invention are administered to the patient at dosage levels of from 0 mg to 600 mg per day. For a normal human adult of approximately 70 kg or body weight, this translates to a dosage of from about 0.5 mg/kg to about 8.0 mg/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of
[4α,6β(E)]-6[-2-[6-Chloro-4-(4-fluorophenyl)-2-methyl-3-quinolinyl]ethenyl]-tetrahydro-4-hydroxy-2H-pyran-2-one

Step 1—Preparation of (2-amino-5-chlorophenyl)-(4-fluorophenyl)methanone p-Fluorobenzoyl chloride (154.0 g, 2.4 equivalents) was heated to 120° C. in a 3-neck, 2-liter round-bottom flask. p-Chloroaniline (51.63 g) was added in portions with stirring and evolution of HCl gas. After addition was complete, the temperature was raised to 180° C. and zinc chloride (66.19 g, 1.2 equivalents) was added in small portions. The resulting mixture was heated to 205° C. for three hours and then allowed to cool to about 150° C. Hydrochloric acid (400 4mL, M) was added and the mixture was heated to reflux and the hot hydrochloric acid decanted. This process was repeated twice to remove excess p-fluorobenzoic acid.

Concentrated hydrochloric acid (500 mL) and glacial acetic acid (500 mL) were added and the resulting mixture was heated under reflux for twenty hours. The dark brown mixture was cooled, concentrated under vacuum, and partitioned between dichloromethane and 1M sodium hydroxide solution. The organic layer was washed with 1M hydrochloric acid, dried over anhydrous magnesium sulfate, and evaporated to give 57.3 g of a brown solid. This material was recrystallized from hexanes to yield 3.65 g of (2-amino-5-chlorophenyl)(-4fluorophenyl)methanone as bright yellow needles.

Proton NMR spectrum (CDCl$_3$): δ 7.7–7.4, (multiplet, 2 protons), δ 7.3–6.9 (multiplet, 4 protons), δ 6.55 (doublet, 1 proton), δ 6.2 (broad singlet, 2 protons).

Step 2—Preparation of 6-chloro-4-(4-fluorophenyl)-2-methyl-3-quinolinecarboxylic acid, ethyl ester To a solution of (2-amino-5-chlorophenyl)-(4-fluorophenyl)methanone (10.0 g) in 100 mL of toluene was added 8.3g (1.6 equivalents) of ethyl acetoacetate and 0.30 g of p-toluenesulfonic acid. The resulting mixture was heated to reflux with azeotropic removal of water. After one and one-half hours, the mixture was cooled to room temperature and concentrated under vacuum. The crude product was purified by flash chromatography over silica gel to give 10.18 g of 6-chloro-4-(4-fluorophenyl)-2-methyl-3-quinolinecarboxylic acid, ethyl ester as an off-white solid.

Proton NMR spectrum (CDCl$_3$): δ 7.9 doublet, 1 proton), δ 7.7–7.0 (multiplet, 6 protons), δ 4.1 (quartet, 2 protons), δ 2.7 (singlet, 3 protons), δ 1.0 (triplet, 3 protons).

Step 3—Preparation of 6-chloro-4-(4-fluorophenyl)-2-methyl-3-quinolinemethanol 6-Chloro-4-(4-fluorophenyl)-2-methyl-3-quinolinecarboxylic acid, ethyl ester (39.51 g) was dissolved in 400 mL of dry dichloromethane in a 2-liter, 3-neck, round-bottom flask under a nitrogen atmosphere. The solution was cooled to −78° C. and a solution of diisobutyl aluminum hydride (2.5 equivalents) in dichloromethane was added dropwise with stirring. After complete addition, the mixture was stirred at −78° C. for one hour.

Sodium sulfate (1.65 g, 2.5 equivalents) in 50 mL of water was then added and the cooling bath was removed. The resulting gelatinous mass was stirred for one-half hour and then filtered through Celite ® and sand. The solid was washed with hot ethyl acetate and the combined filtrates were dried and evaporated to yield 28.72 g of 6-chloro-4-(4-fluorophenyl)-2-methyl3-quinolinemethanol as an off-white solid, mp 173°–175° C.

Proton NMR spectrum (CDCl$_3$) δ 7.8 doublet, 1 proton), 6 7.(doublet of doublets, 1 proton), δ 7.2–7.0 (multiplet, 5 protons), δ4.5 (singlet, 2 protons), δ 2.8 (singlet, 3 protons), and 2.1 (broad singlet, 1 proton).

Step 4—Preparation of 6-chloro-4-(4-fluorophenyl)-2-methyl-3-quinolinecarboxaldehyde To a solution of oxalyl chloride (8.85 mL, 1.1 equivalents) in 150 mL of dry dichloromethane at −78° C. under nitrogen, was added dropwise a solution of dimethylsulfoxide (14.2 mL, 2.2 equivalents) in 125 mL of dichloromethane. After complete addition, the mixture was stirred for five minutes at −78° C. and then a solution of 6-chloro-4-(4-fluorophenyl)-2-methyl-3-quinolinemethanol (27.8 ) in 100 mL of dichloromethane and 50 mL of dimethylsulfoxide was added dropwise. This solution was stirred at −78° C. for one hour, after which triethylamine (64.1 mL, 5.0 equivalents) was added. The cooling bath was removed and 400 mL of saturated ammonium chloride solution was added to the reaction mixture.

The organic layer was separated and the aqueous layer was extracted with additional dichloromethane. The combined organic layers were washed with water and then brine solution. The organic solution was dried over anhydrous magnesium sulfate and evaporated to give 27.63 g of 6-chloro-4-(-fluorophenyl)-2-methyl-3quinolinecarboxaldehyde as a tan solid.

Proton NMR spectrum (CDCl$_3$) δ 9.9 (singlet, 1 proton), δ 7.95 (doublet, 1 proton), δ 7.7 (doublet of doublets, 1 proton), δ 7.5–7.1 (multiplet, 5 protons), and δ 2.9 (singlet, 3 protons).

Step 5—Preparation of (E)-3-[6-chloro-4-(-fluorophenyl)-2-methyl-3-quinolyl]-propenoic acid, methyl ester 6-Chloro-4-(4-fluorophenyl)-2-methyl-3-quinolinecarboxaldehyde (3.60 g) and methyl(triphenylphosphoranylidene) acetate (4.42 g, 1.1 equivalents) were stirred in 100 mL of dichloromethane under a nitrogen atmosphere for five hours at room temperature. The mixture was concentrated under vacuum and the residue was purified by flash chromatography on silica gel to give 3.98 g of (E)-3-[6-chloro-4-(-fluorophenyl)2-methyl-3-quinolyl]propenoic acid, methyl ester as a white solid.

Proton NMR spectrum (CDCl$_3$): δ 7.9 (doublet, 1 proton), 7.7–7.5 (multiplet, 2 protons), 7.3–7.0 (multiplet, 5 protons), 6 .8 (doublet, 1 proton), δ 3.70 (singlet, 3 protons), and 2.8 (singlet, 3 protons).

Step 6—Preparation of (E)--3-[6-chloro-4-(4-fluoro-phenyl)-2-methyl-3-quinolyl]-propenol To a solution of (E-3-[6-chloro-4-(-fluorophenyl)-2-methyl-3-quinolyl]propenoic acid, methyl ester (7.99 g) in 150 mL of dry dichloromethane at −78° C. was added dropwise 2.5 equivalents of a solution of diisobutylaluminum hydride (DIBAL, 1M in dichloromethane) under a nitrogen atmosphere. After complete addition, the cooling bath was removed and the reaction was quenched by the addition of 8.0 g (2.5 equivalents) of a saturated solution of sodium sulfate. The resulting mixture was filtered through Celite® and sand. The solids were washed with hot ethyl acetate and the combined filtrates were dried over anhydrous magnesium sulfate and evaporated to yield 6.59 of (E)-3-[6-chloro-4-(4-fluorophenyl)-2-methyl-3-quinolyl]-propenol as a white solid.

Proton NMR spectrum (CDCl$_3$) δ 7.9 (doublet, 1 proton), 7.5 (doublet of doublets, 1 proton), δ 7.3–7.0 (multiplet, 5 protons), δ 6.4 (doublet, 1 proton), δ 5.6 (doublet of triplets, 1 proton), δ 4.1 (broad singlet, 2 protons), δ 2.7 (singlet, 3 protons), and δ 1.5 (broad triplet, 1 proton).

Step 7—Preparation of (E)-3-[6-chloro-4-(4-fluorophenyl)-2-methyl-3-quinolyl]propenal A solution of oxalyl chloride (2.28 mL, 1.3 equivalents) in 100 mL of dichloromethane was cooled to −78° C. under a nitrogen atmosphere. A solution of dimethylsulfoxide (3.67 mL, 2.6 equivalents) in 75 mL of dichloromethane was added dropwise with stirring. Five minutes after addition was complete, a solution of (E)-3-[6-chloro-4-(4-fluorophenyl)-2-methyl-3-quinolyl]-propenol (6.59 g) in 75 mL of dichloromethane was added dropwise. This solution was stirred at −78° C. for three-quarters of an hour and then 1mL (5.0 equivalents) of triethylamine was added.

The cold bath was removed and the reaction was quenched by the addition of 50 mL of saturated ammonium chloride solution. The organic layer was separated and the aqueous layer was extracted with dichloromethane. The combined organic layers were washed with water and then brine soluion, dried over anhydrous magnesium sulfate, and evaporated to yield 6.14 g of (E-3-[6-chloro-4-(-fluorophenyl)-2-methyl-3-quinolyl]propenal as an orange solid.

Proton NMR spectrum (CDCl$_3$): δ 9.4 (doublet, 1 proton), δ 7.9 (doublet, 1 proton), δ 7.7–7.0 (multiplet, 7 protons), 6.1 (doublet of doublets, 1 proton), and 2.8 (singlet, 3 protons).

Step 8—Preparation of (E)7-[3-[6-chloro-4-(4-fluoro-phenyl)-2-methyl-3-quinolyl]-5-hydroxy-3-oxo-6-heptenoic acid, ethyl ester A solution of ethyl acetoacetate (3.1 g, 1.1 equivalents) in 30 mL of anhydrous tetrahydrofuran was added dropwise with stirring to a suspension of sodium hydride (0.64 g, 1.2 equivalents) in anhydrous tetrahydrofuran at 0° C. under nitrogen. The resulting mixture was stirred at 0° C. for ten minutes, after which n-butyl lithium (10.13 mL, 2M solution in tetrahydrofuran) was added dropwise. The resulting orange solution was stirred for an additional ten minutes and then it was cooled to −78° C. A solution of (E)-3-[6-chloro-4-(4-fluorophenyl)-2-methyl-3-quinolyl]propenal (7.20 g) in 90 mL of anhydrous tetrahydrofuran was added dropwise. The resulting solution was stirred for twenty minutes before the reaction was quenched by the addition of 10 mL of glacial acetic acid and the cooling bath was removed.

The pale orange solution was then stirred at room temperature for two hours after which it was partitioned between diethyl ether and water. The organic layer was separated, washed successively with saturated sodium bicarbonate solution, water, and brine solution, dried, and evaporated. This yielded 8.41 g of crude (E)7-[3-[6-chloro-4-(4-fluorophenyl)-2-methyl-3-quinolyl]-5-hydroxy-3-oxo-6-heptenoic acid, ethyl ester. Flash chromatography on silica gel, eluting with 10% ethyl acetate/toluene, yielded the product as an orange oil.

Proton NMR spectrum (CDCl$_3$): δ 7.9 (doublet, 1 proton), δ 7.5–6.9 (multiplet, 6 protons), δ 6.4 (doublet, 1 proton), δ 5.4 (doublet of doublets, 1 proton), δ 4.5 (broad multiplet, 1 proton), δ 4.1 (quartet, 2 protons), δ 3.3 (singlet, 2 protons), δ 3.2 (broad singlet, 1 proton), δ 2.7 (singlet, 3 protons), δ 2.5 (doublet, 2 protons), and δ 1.2 (triplet, 3 protons).

Step 9—Preparation of [R*,S*(E)]7-[6-chloro-4-(4-fluorophenyl)-2-methyl-3-quinolinyl]-3,5-dihydroxy-6-heptenoic acid, ethyl ester.

Triethylborane (12.6 mL, 1M solution, 1.1 equivalents) was added in a single portion to a solution of 5.22 g of (E)7-[-3-[6-chloro-4-(-fluorophenyl)-2-methyl-3-quinolyl]-5-hydroxy-3-oxo-6-heptenoic acid, ethyl ester and 0.117 g (0.1 equivalents) of pivalic acid in 50 mL of anhydrous tetrahydrofuran under a nitrogen atmosphere. This solution was stirred for five minutes before 20 mL of air was bubbled through the solution. The mixture was then cooled to −78° C. and 10 mL of methanol and 0.48 g (1.1 equivalent) of sodium borohydride were added. This mixture was stirred at −78° C. for six hours and then poured into 50 mL of 30hydrogen peroxide solution at 0° C. This mixture was stirred at room temperature overnight and then diluted with water and extracted with ethyl acetate.

The organic layer was separated, washed extensively with water and brine solution, dried over anhydrous magnesium sulfate and evaporated to yield 4.93 g of [R*,S*(E)] 7-[6-chloro-4-(-fluorophenyl)-2-methyl-3-quinolinyl]-3,5-dihydroxy-6-heptenoic acid, ethyl ester which was used in the next step without further purification.

Step 10—Preparation of [R* ,S* (E)] 7-[6-chloro-4-(4-fluorophenyl)-2-methyl-3-quinolinyl]-3,5-dihydroxy-6-heptenoic acid, and the sodium salt

[R*,S*(E) 7-[6-chloro-4-(-fluorophenyl)-2-methyl-3-quinolinyl]-3,5-dihydroxy-6-heptenoic acid, ethyl ester, (4.93 g) was dissolved in 30 mL of tetrahydrofuran and 10.8 mL of 1M sodium hydroxide solution (1.0 equivalent) was added in one portion at room temperature. Methanol (5 mL) was added to mix the two phases, and this mixture was stirred for three hours at room temperature. The solution was then concentrated to yield crude [R*,S*(E)] 7-[6-chloro-4-(4-fluorophenyl)4-2-methyl-3-quinolinyl]-3,5- dihydroxy-6-heptenoic acid, sodium salt, mp 225°–229° C. (dec). This material was dissolved in water and washed with diethyl ether. The aqueous layer was acidified with 6M hydrochloric acid and then extracted with ethyl acetate. The organic layer was washed with water, dried over anhydrous magnesium sulfate, and evaporated to give 2.73 g of [R*,S*(E) 7-[6-chloro-4-(4-fluorophenyl)-2-methyl-3-quinolinyl]-3,5-dihydroxy-6-heptenoic acid, as a yellow foam.

Step 11—Preparation of [4α,6β(E)]
6-[2-[6-chloro-4-(4-fluorophenyl)-2-methyl-3quinolinyl]-ethenyl]tetrahydro-4-hydroxy-2H-pyran-2-one [R*,S*(E)]

7-[6-Chloro-4-(4-fluorophenyl)-2methyl-3-quinolinyl]-3,5-dihydroxy-6-heptenoic acid (2.73 g) was dissolved in a mixture of 120 mL of toluene and 5 mL of ethyl acetate and the resulting mixture was heated under reflux for five hours with the azeotropic removal of water. The reaction mixture was then concentrated and the residue flash chromatographed on silica gel, eluting with ethyl acetate, to yield 2.03 g of [4α,6β(E)] 6-[2-[6-chloro-4-(4-fluorophenyl)-2-methyl-3-quinolinyl]ethenyl]tetrahydro-4-hydroxy-2H-pyran-2-one as a yellow solid, mp 188°–190° C.

Proton NMR spectrum (CDCl$_3$): δ 8.09 (doublet, 1 proton), δ 7.6 (doublet of doublets, 1 proton), δ 7.4 (doublet, 1 proton), δ 7.3–7.2 (multiplet, 4 protons), δ 6.5 (doublet, 1 proton), δ 5.5 (doublet of doublets, 1 proton), δ 5.2 (multiplet, 1 proton), δ 4.3 (multiplet, 1 proton), δ 2.7 (singlet, 3 protons), δ 2.6 (doublet, 2 protons), and δ 1.8–1.6 (multiplet, 2 protons).

EXAMPLE 2

Preparation of [R*, S*-(E)]
7-[6-Chloro-4-(4-fluorophenyl)-2-(1-methylethyl)-3-quinolinyl]-3,5-dihydroxy-6-heptenoic acid, sodium salt and
[4α,6β(E)]6-[2-[6-Chloro-4-(4-fluorophenyl)-2-(1-methylethyl)-3-quinolinyl]ethenyl]tetrahydro-4-hydroxy-2H-pyran-2-one Employing the general method of Example 1, but employing 4-methyl-3-oxo-pentanoic acid, ethyl ester in Step 2, there was obtained [R*,S*(E)] 7-[6-Chloro-4-(4-fluorophenyl)-2-(1-methylethyl)-3-quinolinyl]-3,5-dihydroxy-6-heptenoic acid, sodium salt, mp >225° C. and [4α,6β(E)] 6-[2-[6-chloro-4-(4-fluorophenyl)-2-(1-methylethyl)-3-quinolinyl]ethenyl]tetrahydro-4-hydroxy-2H-pyran-2-one, mp 173°–175° C.

EXAMPLE 3

Preparation of [R*,S*-(E)]
7-[4-(4Fluorophenyl)-2-(1-methylethyl)-3-quinolinyl]-3,5-dihydroxy-6-heptenoic acid, sodium salt and
[4α,6β(E)]6-[2-[4-(4-Fluorophenyl)-2-(1-methylethyl)-3-quinolinyl]ethenyl]tetrahydro-4-hydroxy-2H-pyran-2-one Employing the general method of Example 2, but employing (2-aminophenyl)-(4-fluorophenyl)methanone (obtained from the hydrogenolysis of (2-amino-5-chlorophenyl)-(4-fluorophenyl)methanone), there was obtained [R*,S*(E)] 7-[4-fluorophenyl-2-(1-methylethyl)-3-quinolinyl]-3,5-dihydroxy-6heptenoic acid, sodium salt, mp 215° C. (dec.) and [4α,6β(E)] 6-[2-[4-(4-fluorophenyl)-2-(1-methylethyl)-3-quinolinyl]ethenyl]-tetrahydro-4hydroxy-2H-pyran-2-one, mp 168°–170° C.

We claim:
1. A compound of structural Formula I

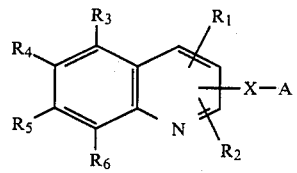

wherein A is

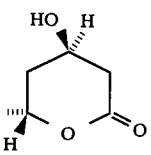

X is —CH2CH2— or —CH=CH—;
R$_1$ and R$_2$ are independently
  hydrogen;
  alkyl of from one to six carbons;
  trifluoromethyl;
  cyclopropyl;
  cyclohexyl;
  cyclohexylmethyl;
  phenyl;
  phenyl substituted with
    fluorine,
    chlorine,
    bromine,
    hydroxy,
    trifluoromethyl,
    alkyl of from one to four carbon atoms, or
    alkoxy of from one to four carbon atoms;
  phenylmethyl;
  phenylmethyl substituted with
    fluorine,
    chlorine,
    bromine,
    hydroxy,
    trifluoromethyl,
    alkyl of from one to four carbon atoms, or
    alkoxy of from one to four carbon atoms;
  2-, 3-, or 4-pyridinyl; or
  2-, 4-, or 5-pyrimidinyl;
R$_3$, R$_4$, R$_5$, R$_6$ are independently selected from
  hydrogen;
  alkyl of from one to six carbon atoms;
  trifluoromethyl;
  cyclopropyl;
  fluorine;
  chlorine;
  bromine;
  hydroxy;
  alkoxy of from one to four carbon atoms;
  cyano;
  nitro;
  amino;
  acetylamino;
  aminomethyl;
  phenyl;
  phenyl substituted with
    fluorine,
    chlorine,
    bromine,
    hydroxy,
    trifluoromethyl, alkyl of from one to four carbon atoms, or alkoxy of from one to four carbon atoms;

phenylmethyl; or phenylmethyl substituted with fluorine, chlorine, bromine, hydroxy, trifluoromethyl, or alkyl of from one to four carbon atoms;

provided that when X is in the 2-position, R1 is hydrogen and is attached in the 4-position;

or a corresponding 3,5-dihydroxyacid of Formula II

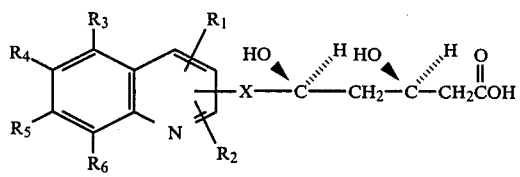

wherein A, X, $R_1$, $R_2$, $R_3$, $R_4$, and $R_5$ are as defined above, or a pharmaceutically acceptable salt thereof.

2. A compound as defined by claim 1 having the structural formula

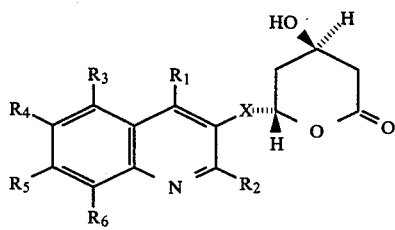

wherein X, $R_1$, $R_2$, $R_3$, $R_4$, $R_5$, and $R_6$ are as defined therein.

3. A compound as defined by claim 1 having the structural formula

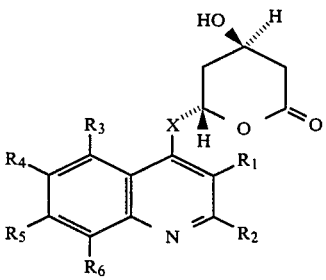

wherein X, $R_1$, $R_2$, $R_3$, $R_4$, $R_5$, and $R_6$ are as defined therein.

4. A compound as defined by claim 1 having structural Formula I.

5. A compound as defined by claim 1 having structural Formula II.

6. A compound as defined by claim 1 wherein X is —CH=CH—.

7. A compound as defined by claim 1 wherein X is —CH$_2$CH$_2$—.

8. A compound as defined by claim 4 having the name [4α,6β(E)]-6-[2-[6-chloro-4-fluorophenyl)-2-methyl-3-quinolinyl]ethenyl]tetrahydro-4-hydroxy-2H-pyran-2-one.

9. A compound as defined by claim 4 having the name [4α,6β(E)]-6-[2-[6-chloro-4-fluorophenyl)-2-(1-methylethyl)-3-quinolinyl]-ethenyl]tetrahydro-4hydroxy-2H-pyran-2-one.

10. A compound as defined by claim 4 having the name [4α,6β(E)]-6-[2-[6-chloro-4-fluorophenyl)-2-(1-methylethyl)-3-quinolinyl]ethenyl]tetrahydro-4-hydroxy-2H-pyran-2-one.

11. A compound as defined by claim 5 having the name [R*, S*-(E)]-7-[6-chloro-4-(4-fluorophenyl)-2-methyl-3quinolinyl]-3,5-dihydroxy-6-heptenoic acid, or a pharmaceutically acceptable salt thereof.

12. A compound as defined by claim 5 having the name [R*, S*-(E)]-7-[6-chloro-4-(4-fluorophenyl)-2-(1-methylethyl)-3-quinolinyl]-3,5-dihydroxy-6-heptenoic acid, or a pharamceutically acceptable salt thereof.

13. A compound as defined by claim 5 having the name [R*,S*-(E)]-7-[4-(4-fluorophenyl)-2-(1-methylethyl)-3-quinolinyl]-3,5-dihydroxy-6heptenoic acid, or a pharmaceutically acceptable salt thereof.

14. A pharmaceutical composition for inhibiting cholesterol biosynthesis comprising an effective amount of a compound as defined by claim 1 in combination with a pharmaceutically acceptable carrier.

15. A method of inhibiting cholesterol biosynthesis in a patient in need of said treatment comprising administering a cholesterol synthesis inhibiting amount of a compound as defined by claim 1 in combination with a pharmaceutically acceptable carrier.

* * * * *

Notice of Adverse Decisions in Interference

In Interference No. 102,648, involving Patent No. 4,761,419, J. A. Picard, B. D. Roth, D. R. Sliskovic, 6-(((SUBSTITUTED)QUINOLINYL)ETHYL)-AND ETHENYL) TETRAHYDRO-4-HYDROXYPYRAN-2-ONE INHIBITORS OF CHOLESTEROL BIOSYNTHESIS, final judgment adverse to the patentees was rendered Apr. 10, 1992, as to claims 1-15.

*(Official Gazette August 25, 1992.)*